(12) United States Patent
Jason

(10) Patent No.: US 12,251,085 B1
(45) Date of Patent: Mar. 18, 2025

(54) SPRING ENABLED EVIDENCE COLLECTION APPARATUS AND METHOD FOR CYLINDRICAL OBJECTS

(71) Applicant: Alexander Jason, Pinole, CA (US)

(72) Inventor: Alexander Jason, Pinole, CA (US)

( * ) Notice: Subject to any disclaimer, the term of this patent is extended or adjusted under 35 U.S.C. 154(b) by 0 days.

(21) Appl. No.: 18/905,133

(22) Filed: Oct. 2, 2024

(51) Int. Cl.
*A61B 10/00* (2006.01)
*B65D 25/02* (2006.01)

(52) U.S. Cl.
CPC .......... *A61B 10/0096* (2013.01); *B65D 25/02* (2013.01)

(58) Field of Classification Search
CPC .............................. B65D 25/02; A61B 10/0096
See application file for complete search history.

(56) References Cited

U.S. PATENT DOCUMENTS

| | | | | |
|---|---|---|---|---|
| 2,451,994 A | * | 10/1948 | Towns | A61B 17/50 604/48 |
| 2,492,576 A | * | 12/1949 | James | B25B 23/106 81/448 |
| 4,037,866 A | * | 7/1977 | Price | A61F 9/0061 294/1.2 |
| 8,770,642 B1 | * | 7/2014 | Jason | B25B 9/02 294/93 |
| 2012/0220042 A1 | * | 8/2012 | Sangha | G01N 1/02 422/411 |

* cited by examiner

*Primary Examiner* — Stephen A Vu
(74) *Attorney, Agent, or Firm* — Sam Pierce

(57) ABSTRACT

An evidence collection apparatus and method for collecting and preserving cylindrical objects, such as spent cartridge casings, while maintaining trace evidence integrity. The apparatus comprises a handle member, an evidence retention device with a pair of arms having bent distal ends forming prongs to retain the inner perimeter of a cylindrical object, and a spring-tweezer mechanism for securely grasping the object. A protective tube coupled to the handle member stores the collected evidence. The method involves inserting the retention device into the cylindrical object, actuating the spring-tweezer mechanism, removing the object from the crime scene, and securing it in the protective tube for transport and analysis. The invention enables secure evidence collection and preservation, minimizing contamination risks.

18 Claims, 5 Drawing Sheets

SPRING ENABLED EVIDENCE COLLECTION APPARATUS AND METHOD FOR CYLINDRICAL OBJECTS

BACKGROUND

The present invention relates generally to the field of forensic evidence collection and preservation. More specifically, the present invention pertains to an improved evidence collection apparatus and method for collecting and preserving trace evidence from cylindrical objects, such as spent cartridge casings, while minimizing contamination and maintaining the integrity of the collected evidence for subsequent analysis.

Proper collection and preservation of physical evidence from crime scenes is of utmost importance in forensic investigations. Trace evidence, such as DNA, fingerprints, and gunshot residue, can provide crucial links between a suspect, victim, and the crime scene. However, the collection process itself can be challenging, as it requires meticulous handling procedures to avoid contamination and ensure the admissibility of the evidence in court.

Cylindrical objects, particularly spent cartridge casings ejected from firearms, are commonly encountered at crime scenes involving shooting incidents. The microscopic markings imparted on the casings by the firearm during the firing and ejection process can be used to identify the specific weapon. Moreover, the casings may retain valuable trace evidence on their surfaces from the shooter's hands or the environment. Therefore, careful collection, transport and preservation of spent cartridge casings is paramount.

Conventional methods for collecting cylindrical objects, such as spent casings, often involve the use of ordinary tweezers or forceps. However, these tools can potentially disturb or dislodge trace evidence on the object's surface during the collection process. Additionally, they offer limited control and precision, especially when dealing with small, lightweight objects like casings.

To address these limitations, various specialized evidence collection devices have been developed. For instance, U.S. Pat. No. 8,770,642 to Jason discloses an evidence collection device comprising a handle member with an evidence retention device extending therefrom. The retention device includes a pair of arms with bent distal ends forming prongs to retain the inner perimeter of a cylindrical object. A container member is provided to receive the handle portion and secure the collected evidence. While this device improves upon traditional collection methods, it lacks features for enhanced evidence preservation and ease of operation.

Another example is the specimen collection apparatus described in international patent application WO2007084454A2 and European patent EP1976635B1. This apparatus includes a handle member with an evidence retention device having two arms with bent distal ends forming prongs. The prongs are configured to retain the inner perimeter of a cylindrical object. However, this device does not provide a secure means for grasping and manipulating the collected object during the collection process.

In light of the limitations of the prior art, there exists a need for an improved evidence collection device and method that enables the secure collection, retention, and preservation of cylindrical objects, such as spent cartridge casings, while minimizing the risk of contamination and loss of trace evidence. The present invention addresses this need by providing an evidence collection apparatus with enhanced features for evidence retention, manipulation, and preservation, as well as a systematic method for its use in forensic evidence collection procedures.

SUMMARY

The present invention is directed to an evidence collection apparatus and method for collecting and preserving cylindrical objects, such as spent cartridge casings, from crime scenes while maintaining the integrity of trace evidence on the object's surfaces.

In one aspect, the invention provides an evidence collection device comprising a handle member, a-spring-tweezer mechanism extending from the handle member, and a spring-tweezer mechanism disposed on the handle member. The spring-tweezer mechanism includes a pair of arms with bent distal ends forming prongs adapted to retain the inner perimeter of a cylindrical object. The spring-tweezer mechanism is configured to grasp and securely hold the cylindrical object during the collection process. A protective tube is coupled to the handle member for securely storing the collected object for transport and subsequent analysis.

In another aspect, the invention provides a method for collecting and preserving evidence using the evidence collection device. The method involves inserting the spring-tweezer mechanism into a cylindrical object, actuating the spring-tweezer mechanism to grasp the object, removing the object from the crime scene, and securing it in the protective tube for transport and further forensic analysis.

The evidence collection apparatus and method of the present invention offer several advantages over the prior art. The spring-tweezer mechanism allows for secure grasping and manipulation of the cylindrical object, reducing the risk of contamination and loss of trace evidence. The protective tube provides a sealed environment for storing and transporting the collected evidence. Additionally, the ergonomic design of the handle member facilitates single-handed operation and precise control during the collection process.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

Additional features and advantages of the invention will be set forth in the description which follows, and in part will be obvious from the description, or may be learned by the practice of the invention. These and other features of the present invention will become more fully apparent from the following description, or may be learned by the practice of the invention as set forth hereinafter.

BRIEF DESCRIPTION OF THE DRAWINGS

The various exemplary embodiments of the present invention. which will become more apparent as the description proceeds, are described in the following detailed description in conjunction with the accompanying drawings, in which.

DETAILED DESCRIPTION

Figure 1:
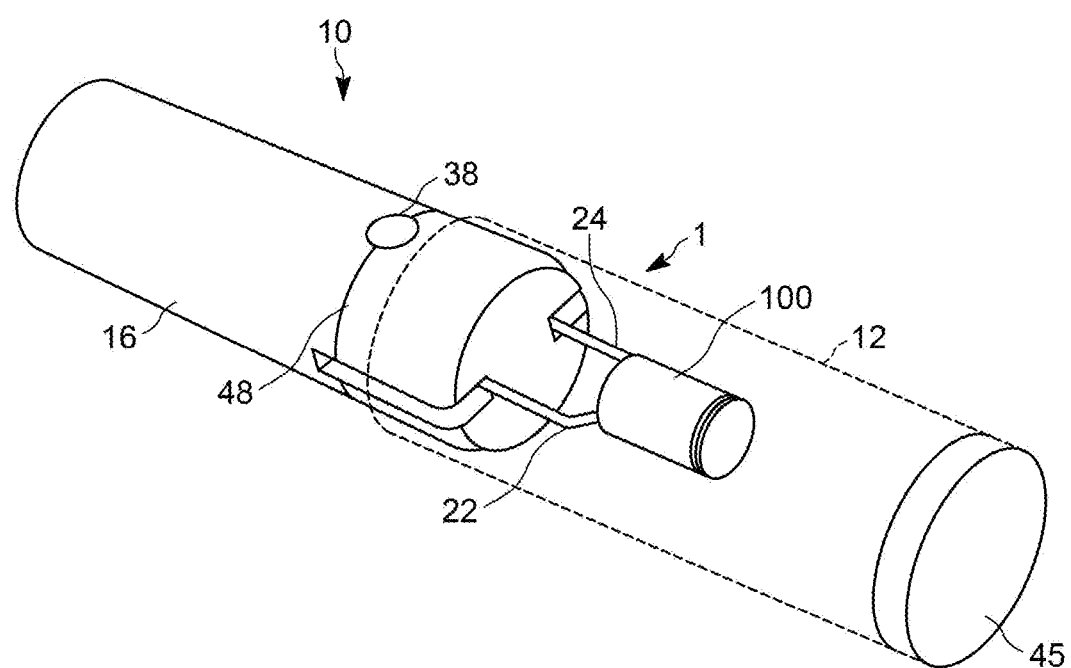
FIG. 1 is a perspective view of an evidence collection apparatus according to an embodiment of the present invention.

In the following detailed description of the preferred embodiments, reference is made to the accompanying drawings, which form a part hereof and show, by way of illustration, specific embodiments in which the invention may be practiced. It is to be understood that other embodiments may be used and structural or logical changes may be made without departing from the scope of the present invention. The following detailed description, therefore, is not to be taken in a limiting sense, and the scope of the present invention is defined by the appended claims.

The following description is provided as an enabling teaching of the present systems, and/or methods in its best, currently known aspect. To this end, those skilled in the relevant art will recognize and appreciate that many changes can be made to the various aspects of the present systems described herein, while still obtaining the beneficial results of the present disclosure. It will also be apparent that some of the desired benefits of the present disclosure can be obtained by selecting some of the features of the present disclosure without utilizing other features.

Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

The terms "a" and "an" and "the" and similar references used in the context of describing a particular embodiment of the present invention (especially in the context of certain claims) are construed to cover both the singular and the plural. The recitation of ranges of values herein is merely intended to serve as a shorthand method of referring individually to each separate value falling within the range. Unless otherwise indicated herein. each individual value is incorporated into the specification as if it were individually recited herein.

All systems described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application. Thus, for example, reference to "an element" can include two or more such elements unless the context indicates otherwise.

As used herein, the terms "optional" or "optionally" mean that the subsequently described event or circumstance can or cannot occur, and that the description includes instances where said event or circumstance occurs and instances where it does not.

The word or as used herein means any one member of a particular list and also includes any combination of members of that list. Further, one should note that conditional language, such as, among others, "can," "could," "might." or "may." unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

FIG. 1 is a perspective view of an evidence collection apparatus 1 according to an embodiment of the present invention. The evidence collection apparatus 1 includes a handle member 10 and a protective tube 12 removably couplable to the handle member 10.

The handle member 10 comprises a spring-tweezer mechanism 14 extending from a handle portion 16. The spring-tweezer mechanism 14 includes a first arm 22 and a second arm 24 fabricated from a single piece of shape-memory alloy wire 18. A distal end of the first arm 22 is bent to form a first prong 30, with a portion of the first prong 30 extending inward past an axial line of the first arm 22. Similarly, a distal end of the second arm 24 is bent to form a second prong 32. The shape-memory properties of the wire 18 allow the first and second arms 22, 24 to return to their original undeformed shape after being deformed during use. This enables the spring-tweezer mechanism 14 to securely grasp and retain an inner perimeter of a cylindrical object, such as a cartridge casing 100, while preserving any trace evidence on the surfaces of the cartridge casing 100.

The handle member 10 further includes a spring-tweezer mechanism 14 for selectively grasping and releasing the cylindrical object. The spring-tweezer mechanism 14 comprises a first tweezer arm 22 and a second tweezer arm 24 coupled to the handle portion 16. A spring member 20, such as a torsion spring or leaf spring, is disposed between the first and second tweezer arms 22, 24. The spring member 20 biases the distal ends of the tweezer arms 22, 24 together to grasp the cylindrical object. The tweezer spring arms are squeezed together to allow insertion into a casing. The engineered strength of the tweezer spring is sufficient (when the finger applied squeeze force stops) is sufficient to grasp the casing from the inside. The present invention has sharpened steel tips which push into and firmly engage the softer brass or aluminum of the casings. is coupled to the handle portion 16 and operably connected to the tweezer arms 22, 24. User actuation (by squeezing the tweezer spring) moves the distal ends of the tweezer arms 22, 24 apart to release the cylindrical object.

The handle portion 16 includes ergonomic features to facilitate single-handed operation of the evidence collection apparatus 1. For example, the handle portion 16 may have a textured gripping surface 48 to improve user grip and control. The handle portion 16 snaps on to selectively lock and release the protective tube 12. The handle portion 16 also includes an adhesive tape which wraps around and increases the security of the connection between the tube and the handle.

The protective tube 12 comprises a translucent or transparent tubular body having an open proximal end and a closed distal end 45. The tubular body is sized to receive and securely retain the cylindrical object grasped by the spring-tweezer mechanism 14. The tubular body may be fabricated from a clear, translucent, or opaque plastic material that allows visual inspection of the contained cylindrical object without opening the protective tube 12.

Figure 2:
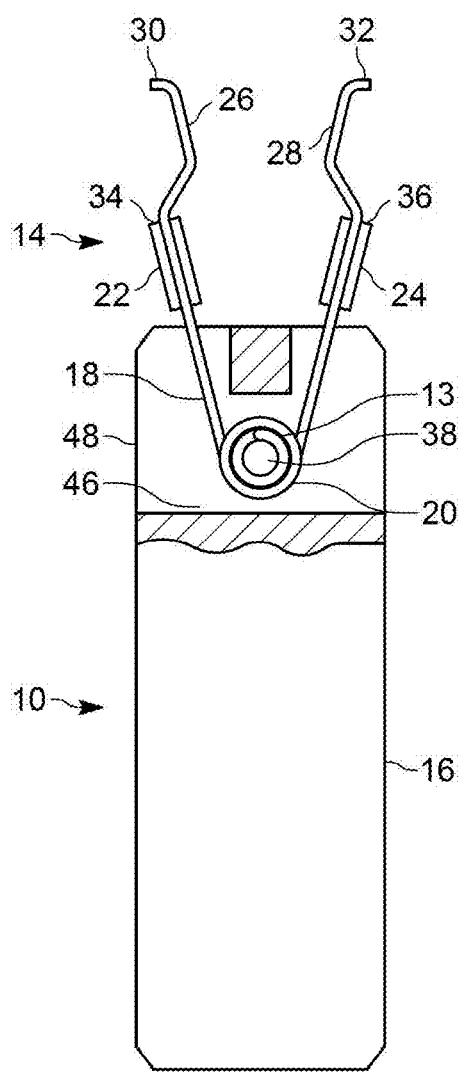
FIG. 2 shows the spring-tweezer mechanism in greater detail.

FIG. 2 shows the spring-tweezer mechanism 14 in greater detail. The distal ends of the first and second arms 22, 24 are offset inward to form first and second offset portions 26, 28 respectively. This offset configuration allows the prongs 30, 32 to securely grasp the inner perimeter of the cartridge casing 100 without slippage.

Figure 3:
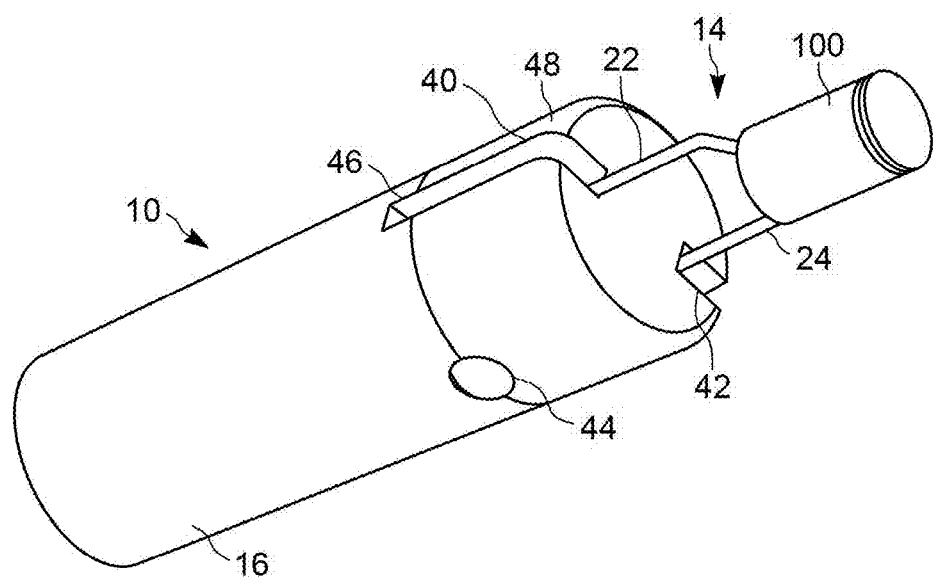
FIG. 3 depicts the handle portion of the handle member.

FIG. 3 depicts the handle portion 16 of the handle member 10. The handle portion 16 includes a retention dowel 38 inserted into a dowel hole 44 formed transversely through the handle portion 16. First and second clearance slots 40, 42 are formed in the sides and end of the handle portion 16 to provide clearance for the first and second arms 22, 24 of the spring-tweezer mechanism 14. A through slot 46 at the end of the clearance slots 40, 42 provides clearance for the spring member 20. The retention dowel 38 passes through the spring member 20 to retain the spring-tweezer mechanism 14 on the handle portion 16.

Figure 4:
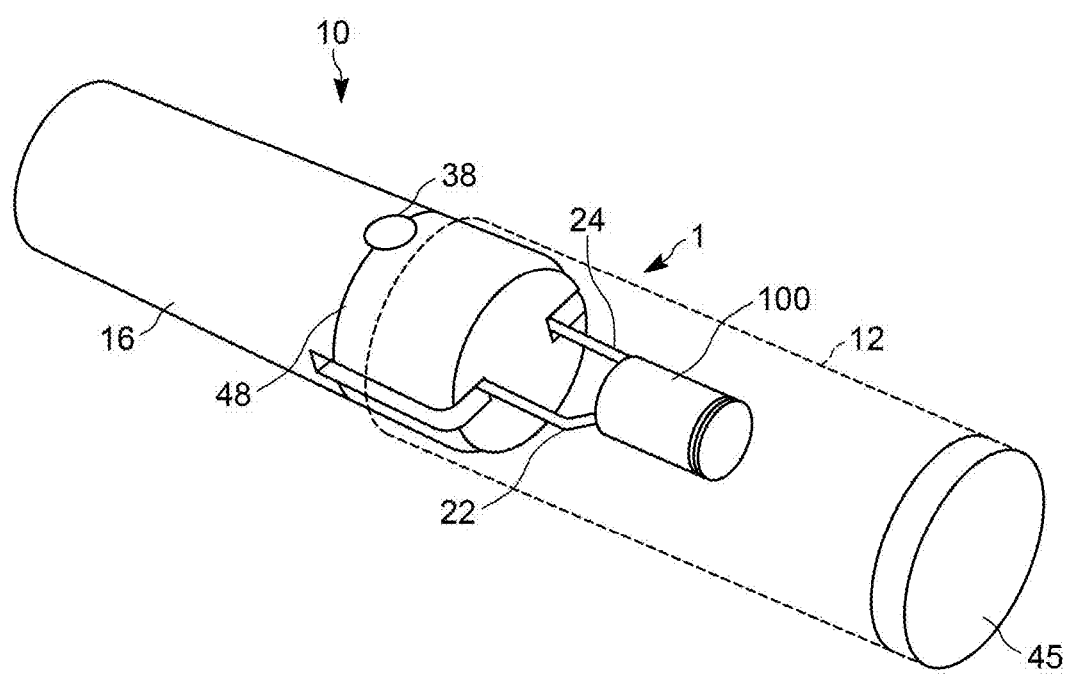
FIG. 4 shows the evidence collection apparatus in an assembled state, with the protective tube coupled to the handle member.

FIG. 4 shows the evidence collection apparatus 1 in an assembled state, with the protective tube 12 coupled to the handle member 10. In use, the first and second arms 22, 24 of the spring-tweezer mechanism 14 are inserted into the cartridge casing 100 and allowed to expand outward to grasp the inner perimeter of the casing 100. The handle portion 16 is then inserted into the protective tube 12, suspending the cartridge casing 100 within the tube 12 without contacting the inner walls. This suspension prevents loss or contamination of trace evidence on the casing 100 during storage and transport.

The evidence collection apparatus 1 may incorporate additional features to enhance its functionality and usability. For example, the spring-tweezer mechanism 14 may include adjustable tension control to accommodate cylindrical objects of varying sizes and materials. The protective tube 12 may be provided with tamper-evident seals or unique identification markings to maintain the chain of custody. The handle member 10 may incorporate built-in illumination, such as LED lights, to assist in locating and collecting evidence in low-light conditions.

Figure 5:
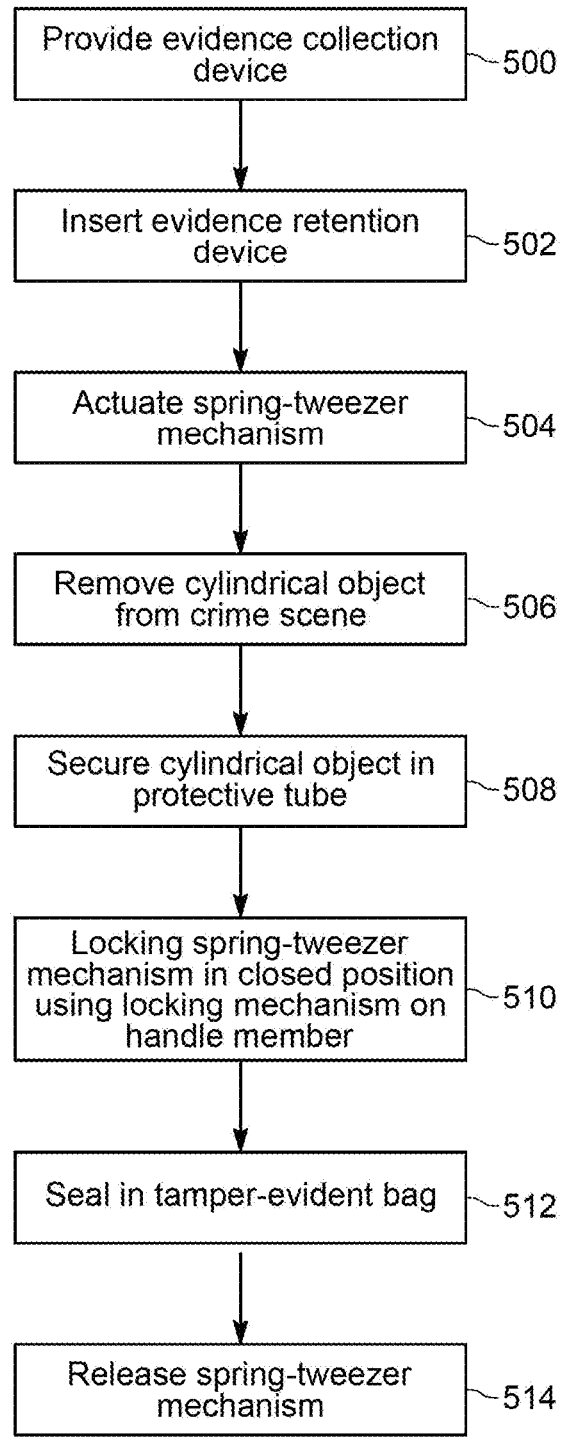
FIG. 5 is a flow chart illustrating the operation of the evidence collection device.

FIG. 5 is a flow chart illustrating the operation of the evidence collection device 1 for collecting and preserving evidence according to the method of the present invention. The method begins at step 500 by providing the evidence collection device 1.

The evidence collection device 1 includes the handle member 10 having the spring-tweezer mechanism 14 extending from the handle portion 16. The spring-tweezer mechanism 14 is formed from the shape-memory alloy wire 18 and includes the first arm 22 and the second arm 24. A distal end of the first arm 22 is bent to form the first prong 30, while a distal end of the second arm 24 is bent to form the second prong 32. The first prong 30 has a portion extending inward past an axial line of the first arm 22. The spring-tweezer mechanism 14 is configured to retain an inner perimeter of a cylindrical object, such as the cartridge casing 100.

The handle member 10 further includes the spring-tweezer mechanism 14 with the first tweezer arm 22 and the second tweezer arm 24 biased toward each other in a closed position by the spring member 20. The first and second tweezer arms 22, 24 have the textured? gripping surfaces 48 at their distal ends to conform to and grasp an outer surface of the cylindrical object.

At step 502, the spring-tweezer mechanism 14 is inserted into the cylindrical object such that the first and second prongs 30, 32 engage the inner perimeter of the cylindrical object.

At step 504, the spring-tweezer mechanism 14 is actuated to cause the first and second tweezer arms 22, 24 to separate to an open position to receive and grasp the cylindrical object.

At step 506, the cylindrical object is removed from the crime scene while spring-tweezer mechanism 14 acts to preserve any trace evidence on the surfaces of the cylindrical object.

At step 508, the cylindrical object is secured in the protective tube 12 coupled to the handle member 10 for transport and subsequent forensic analysis. The protective tube 12 may be transparent to allow visual inspection and have the closed distal end 45.

The embodiments described herein are given for the purpose of facilitating the understanding of the present invention and are not intended to limit the interpretation of the present invention. The respective elements and their arrangements, materials, conditions, shapes, sizes, or the like of the embodiment are not limited to the illustrated examples but may be appropriately changed. Further, the constituents described in the embodiment may be partially replaced or combined together.

What is claimed is:

1. A method for collecting and preserving evidence comprising:

providing an evidence collection device, said evidence collection device including:

a handle member having a spring-tweezer mechanism and a handle portion, said spring-tweezer mechanism extending from said handle portion and including a first tweezer arm and a second tweezer arm, a distal end of said first arm biased away from a distal end of said second tweezer arm, said distal end of said first tweezer arm bent to form a first prong, said distal end of said second tweezer arm bent to form a second prong, a portion of said first prong extending inward past an axial line of said first tweezer arm, wherein said spring-tweezer mechanism is configured to retain an inner perimeter of a cylindrical object; and a spring-tweezer mechanism disposed on said handle member, said spring-tweezer mechanism configured to grasp and retain the cylindrical object, wherein said handle member further comprises a locking mechanism configured to lock said spring-tweezer mechanism in said closed position to securely retain the cylindrical object;

inserting said spring-tweezer mechanism into the cylindrical object such that said first and second prongs engage the inner perimeter of the cylindrical object;

actuating said spring-tweezer mechanism to grasp the cylindrical object;

removing the cylindrical object from a crime scene while preserving trace evidence on surfaces of the cylindrical object; and securing the cylindrical object in a protective tube coupled to said handle member for transport and subsequent forensic analysis.

2. The method of claim 1, wherein said spring-tweezer mechanism comprises a first tweezer arm and a second tweezer arm, said first and second tweezer arms biased toward each other in a closed position, wherein actuating said spring-tweezer mechanism causes said first and second tweezer arms to separate to an open position configured to receive the cylindrical object.

3. The method of claim 2, wherein said first and second tweezer arms each comprise a gripping portion disposed at a distal end thereof, said gripping portions configured to conform to an outer surface of the cylindrical object when in said closed position.

4. The method of claim 1, wherein said handle member further comprises a release mechanism configured to release said spring-tweezer mechanism from said closed position to said open position to release the cylindrical object.

5. The method of claim 1, wherein said protective tube is removably coupled to said handle member, said protective tube comprising a transparent material configured to allow visual inspection of the cylindrical object retained therein.

6. The method of claim 1, wherein said handle member further comprises a label portion configured to receive identifying information related to the cylindrical object and said crime scene.

7. The method of claim 1, wherein said first and second tweezer arms of said spring-tweezer mechanism are composed of a shape-memory material configured to return said first and second prongs to an original position after deformation.

8. The method of claim 1, wherein said handle portion of said handle member comprises an ergonomic grip configured to facilitate single-handed operation of said evidence collection device.

9. The method of claim 1, further comprising:
sealing said protective tube with said cylindrical object retained therein in a tamper-evident bag; and
labeling said tamper-evident bag with identifying information related to said cylindrical object and said crime scene.

10. The method of claim 1, wherein said first and second tweezer arms are fabricated from a single piece of wire.

11. The method of claim 1, wherein said protective tube comprises:
a tubular body having an open proximal end and a closed distal end; and
a cap removably couplable to said open proximal end of said tubular body to seal the cylindrical object within said protective tube.

12. An evidence collection apparatus comprising:
a handle member including a spring-tweezer mechanism and a handle portion, said spring-tweezer mechanism extending from said handle portion and including a first tweezer arm and a second tweezer arm, a distal end of said first tweezer arm biased away from a distal end of said second tweezer arm, said distal end of said first tweezer arm bent to form a first prong, said distal end of said second tweezer arm bent to form a second prong, a portion of said first prong extending inward past an axial line of said first tweezer arm, wherein said spring-tweezer mechanism is configured to retain an inner perimeter of a cylindrical object;
a spring-tweezer mechanism disposed on said handle member, said spring-tweezer mechanism configured to selectively grasp and release the cylindrical object upon actuation, wherein said handle member further comprises a locking mechanism configured to lock said spring-tweezer mechanism in said closed position to securely retain the cylindrical object; and
a protective tube removably couplable to said handle member, said protective tube configured to securely retain the cylindrical object for transport and subsequent forensic analysis;
wherein said first and second tweezer arms are fabricated from a single piece of wire, and wherein said spring-tweezer mechanism is configured to preserve trace evidence on surfaces of the cylindrical object during collection from a crime scene.

13. The evidence collection apparatus of claim 12, wherein said spring-tweezer mechanism comprises:
a first tweezer arm coupled to said handle member;
a second tweezer arm coupled to said handle member opposite said first tweezer arm; and
a spring member disposed between said first and second tweezer arms, wherein said spring member biases distal ends of said first and second tweezer arms together to grasp the cylindrical object.

14. The evidence collection apparatus of claim 13, further comprising an actuator coupled to said handle member and operably connected to said first and second tweezer arms, wherein user actuation of said actuator moves said distal ends of said first and second tweezer arms apart to release the cylindrical object.

15. The evidence collection apparatus of claim 14, wherein said tubular body is at least partially transparent to allow visual inspection of the cylindrical object contained therein without opening said protective tube.

16. The evidence collection apparatus of claim 12, wherein said first and second tweezer arms of said spring-tweezer mechanism are composed of a shape-memory alloy configured to return said first and second tweezer arms to an original undeformed shape after being deformed.

17. The evidence collection apparatus of claim 12, wherein said handle portion of said handle member comprises a textured gripping surface to improve user grip and control of said evidence collection apparatus during use.

18. The evidence collection apparatus of claim 12, wherein said first and second tweezer arms of said spring-tweezer mechanism are composed of a shape-memory material configured to return said first and second prongs to an original position after deformation.

* * * * *